(12) United States Patent
Ohno et al.

(10) Patent No.: US 11,889,984 B2
(45) Date of Patent: Feb. 6, 2024

(54) CAMERA HEAD

(71) Applicant: Sony Olympus Medical Solutions Inc., Tokyo (JP)

(72) Inventors: Atsuomi Ohno, Tokyo (JP); Kohtaro Amano, Tokyo (JP)

(73) Assignee: SONY OLYMPUS MEDICAL SOLUTIONS INC., Tokyo (JP)

(*) Notice: Subject to any disclaimer, the term of this patent is extended or adjusted under 35 U.S.C. 154(b) by 190 days.

(21) Appl. No.: 17/134,533

(22) Filed: Dec. 28, 2020

(65) Prior Publication Data

US 2021/0219822 A1 Jul. 22, 2021

(30) Foreign Application Priority Data

Jan. 16, 2020 (JP) ................................. 2020-005505

(51) Int. Cl.
*A61B 1/00* (2006.01)
*A61B 1/05* (2006.01)

(52) U.S. Cl.
CPC ...... *A61B 1/00105* (2013.01); *A61B 1/00128* (2013.01); *A61B 1/00195* (2013.01); *A61B 1/05* (2013.01)

(58) Field of Classification Search
CPC ............ A61B 1/00105; A61B 1/00128; A61B 1/00195; A61B 1/05; A61B 1/042
See application file for complete search history.

(56) References Cited

U.S. PATENT DOCUMENTS

| | | | | |
|---|---|---|---|---|
| 5,368,014 | A * | 11/1994 | Anapliotis | A61B 1/00135 600/162 |
| 6,254,061 | B1 * | 7/2001 | Levine | A61B 1/00135 251/324 |
| 7,924,515 | B2 * | 4/2011 | Plangger | G02B 23/16 359/829 |
| 2006/0215013 | A1 * | 9/2006 | Jongsma | A61B 1/00195 348/E7.087 |
| 2013/0342906 | A1 * | 12/2013 | Dahmen | G02B 23/2476 359/513 |
| 2017/0319191 | A1 * | 11/2017 | Kiedrowski | A61B 1/00137 |

FOREIGN PATENT DOCUMENTS

| | | |
|---|---|---|
| JP | H07047054 A | 2/1995 |
| JP | H10234660 A | 9/1998 |
| JP | H10243917 A | 9/1998 |
| JP | H11337846 A | 12/1999 |
| JP | 2007502627 A | 2/2007 |
| WO | WO-2019026385 A1 | 2/2019 |

* cited by examiner

*Primary Examiner* — John P Leubecker
*Assistant Examiner* — Li-Ting Song
(74) *Attorney, Agent, or Firm* — XSENSUS LLP (57) ABSTRACT

A camera head includes: a mounting portion having an abutting surface on which an eyepiece portion of an endoscope abuts in a direction along an optical axis of a subject image emitted from the eyepiece portion; and an elastic portion including elastic material and detachably attached to the mounting portion, the elastic portion being configured to sandwich the eyepiece portion with the abutting surface, and bias the eyepiece portion toward the abutting surface.

9 Claims, 11 Drawing Sheets

CAMERA HEAD

CROSS-REFERENCE TO RELATED APPLICATION

This application claims priority from Japanese Application No. 2020-005505, filed on Jan. 16, 2020, the contents of which are incorporated by reference herein in its entirety.

BACKGROUND

The present disclosure relates to a camera head.

In the related art, there has been known a camera head that is detachably connected to an eyepiece portion of an endoscope and that captures a subject image emitted from the eyepiece portion (e.g., see JP 2017-6207 A). The endoscope is inserted into a subject, and captures a subject image from the subject.

In such a camera head, a portion that is detachably connected to an eyepiece portion (hereinafter, referred to as an endoscope connection portion) commonly has the following configuration.

An endoscope connection portion includes a mount, a ring, and a locking member.

The mount has a substantially columnar shape. A mounting recess into which an eyepiece portion may be fitted is provided in the mount. Furthermore, a through hole penetrating from an outer peripheral surface to the mounting recess is provided in the mount.

The ring is provided so as to face the outer peripheral surface of the mount. Then, the ring rotates around the central axis of the mount in response to user operation.

The locking member is provided between the mount and the ring, and protrudes into and withdraws from the mounting recess via the through hole.

That is, when connecting a camera head (endoscope connection portion) to an endoscope (eyepiece portion), an operator fits the eyepiece portion into the mounting recess, rotates the ring, and causes the locking member to protrude into the mounting recess, thereby locking the fitted state.

SUMMARY

The mount and the ring, however, include metal material in the above-described endoscope connection portion. Unfortunately, this hinders reduction in weight of a camera head.

Furthermore, the ring may not be detached from the mount in the above-described endoscope connection portion. Unfortunately, this makes it difficult to clean, for example, a gap between the mount and the ring when the camera head is cleaned.

There is a need for a technique capable of improving cleaning performance while reducing the weight.

According to one aspect of the present disclosure, there is provided a camera head including: a mounting portion having an abutting surface on which an eyepiece portion of an endoscope abuts in a direction along an optical axis of a subject image emitted from the eyepiece portion; and an elastic portion including elastic material and detachably attached to the mounting portion, the elastic portion being configured to sandwich the eyepiece portion with the abutting surface, and bias the eyepiece portion toward the abutting surface.

DETAILED DESCRIPTION

Hereinafter, embodiments for carrying out the disclosure (hereinafter, embodiments) will be described with reference to the drawings. Note that the disclosure is not limited by the embodiments described below. Moreover, in the description of the drawings, the same signs are given to the same parts.

Figure 1:
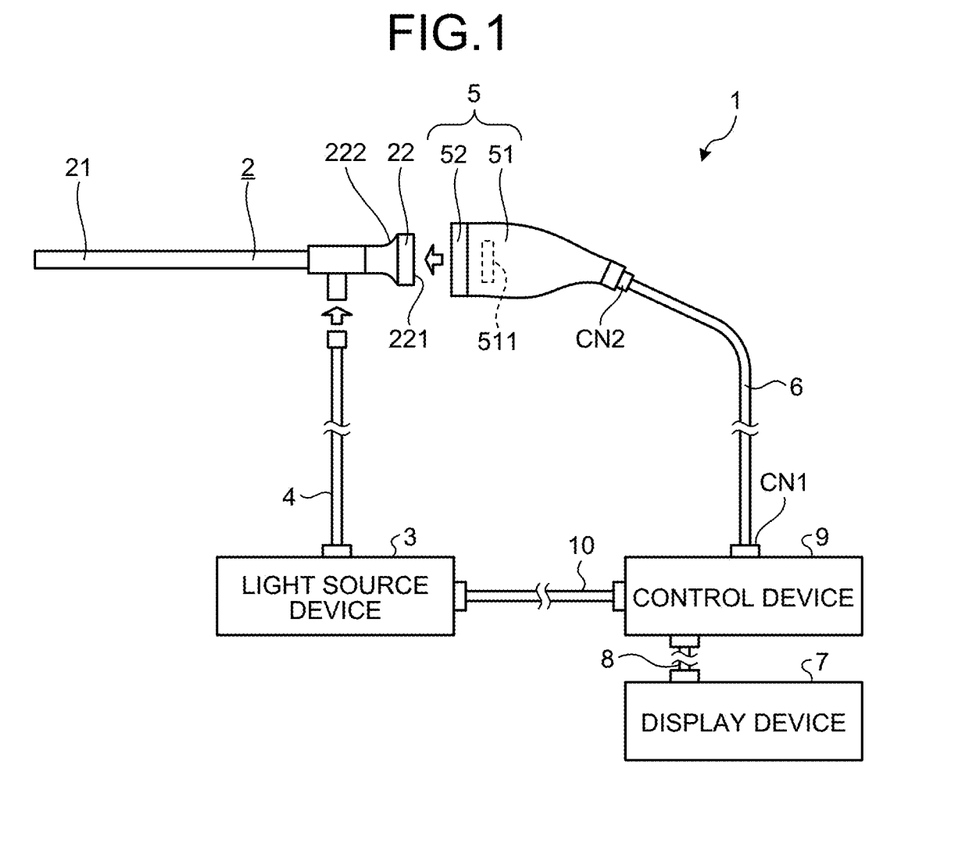
FIG. 1 illustrates a schematic configuration of a medical observation system according to a first embodiment.

FIG. 1 illustrates a schematic configuration of a medical observation system 1 according to a first embodiment.

The medical observation system 1 is used in the medical field to observe the inside of a living body. As illustrated in FIG. 1, the medical observation system 1 includes an endoscope 2, a light source device 3, a light guide 4, a camera head 5, a first transmission cable 6, a display device 7, a second transmission cable 8, a control device 9, and a third transmission cable 10.

The endoscope 2 is a rigid endoscope. That is, the endoscope 2 has an elongated shape. The endoscope 2 is entirely hard, or has a soft part and the other hard part. The endoscope 2 is inserted into a living body. As illustrated in FIG. 1, the endoscope 2 includes an insertion portion 21 and an eyepiece portion 22.

The insertion portion 21 linearly extends, and is inserted into a living body. An optical system (not illustrated) is provided in the insertion portion 21. The optical system includes one or a plurality of lenses and collects a subject image The eyepiece portion 22 is provided at the proximal end of the insertion portion 21. An eyepiece optical system (not illustrated) is provided in the eyepiece portion 22. The eyepiece optical system emits a subject image that has been collected by the optical system in the insertion portion 21 from the eyepiece portion 22 to the outside.

Note that the detailed shape of the eyepiece portion 22 will be described later.

One end of the light guide 4 is connected to the light source device 3. The light source device 3 supplies light for illuminating the inside of a living body to one end of the light guide 4 under the control of the control device 9.

Note that, although the light source device 3 is configured separately from the control device 9 in the first embodiment, this is not a limitation. A configuration in which the light source device 3 is provided inside the control device 9 may be adopted.

One end of the light guide 4 is detachably connected to the light source device 3, and the other end thereof is detachably connected to the endoscope 2. Then, the light guide 4 transmits light supplied from the light source device 3 from one end to the other end, and supplies the light to the endoscope 2. The light supplied to the endoscope 2 is emitted from the distal end of the insertion portion 21, and applied to the inside of the living body. The light (subject image) applied to the inside of the living body and reflected in the living body is collected by the optical system in the insertion portion 21.

As illustrated in FIG. 1, the camera head 5 includes a sealing portion 51 and an endoscope connection portion 52. For example, an imaging element 511 is housed in the sealing portion 51 in an airtight or watertight manner. The endoscope connection portion 52 is provided on the sealing portion 51, and detachably connected to the eyepiece portion 22 of the endoscope 2. Here, the imaging element 511 is provided on the optical axis (on later-described central axes Ax1 and Ax2) of a subject image emitted from the eyepiece portion 22 of the endoscope 2. Then, the camera head 5 captures the subject image collected by the endoscope 2 with the imaging element 511, and outputs an image signal (RAW signal) obtained by the capturing under the control of the control device 9. The image signal is, for example, an image signal of 4K or more.

Note that the detailed configuration of the endoscope connection portion 52 will be described later.

One end of the first transmission cable 6 is detachably connected to the control device 9 via a connector CN1 (FIG. 1), and the other end thereof is detachably connected to the camera head 5 via a connector CN2 (FIG. 1). Then, the first transmission cable 6 transmits, for example, an image signal output from the camera head 5 to the control device 9 while transmitting, for example, a control signal, a synchronization signal, a clock, and electric power output from the control device 9 to the camera head 5.

Note that, for example, an image signal may be transmitted from the camera head 5 to the control device 9 via the first transmission cable 6 in a form of optical signal, or may be transmitted in a form of electric signal. A control signal, a synchronization signal, and a clock may also be transmitted similarly from the control device 9 to the camera head 5 via the first transmission cable 6.

The display device 7 includes a display formed of, for example, liquid crystal or organic electro luminescence (EL). The display device 7 displays an observation image based on a video signal from the control device 9 under the control of the control device 9.

One end of the second transmission cable 8 is detachably connected to the display device 7, and the other end thereof is detachably connected to the control device 9. Then, the second transmission cable 8 transmits a video signal that has been processed by the control device 9 to the display device 7.

The control device 9 includes, for example, a central processing unit (CPU). The control device 9 comprehensively controls the operations of the light source device 3, the camera head 5, and the display device 7.

Specifically, the control device 9 generates a video signal by performing various pieces of processing on the image signal acquired from the camera head 5 via the first transmission cable 6, and outputs the video signal to the display device 7 via the second transmission cable 8. Then, the display device 7 displays an observation image based on the video signal. Furthermore, the control device 9 outputs, for example, a control signal to the camera head 5 and the light source device 3 via the first and third transmission cables 6 and 10.

One end of the third transmission cable 10 is detachably connected to the light source device 3, and the other end thereof is detachably connected to the control device 9. Then, the third transmission cable 10 transmits a control signal from the control device 9 to the light source device 3.

Note that a "distal end side" described below means the distal end side (left side in FIGS. 1 to 6) of the endoscope 2. Furthermore, a "proximal end side" means the side (right side in FIGS. 1 to 6) away from the distal end of the endoscope 2.

Figure 2:
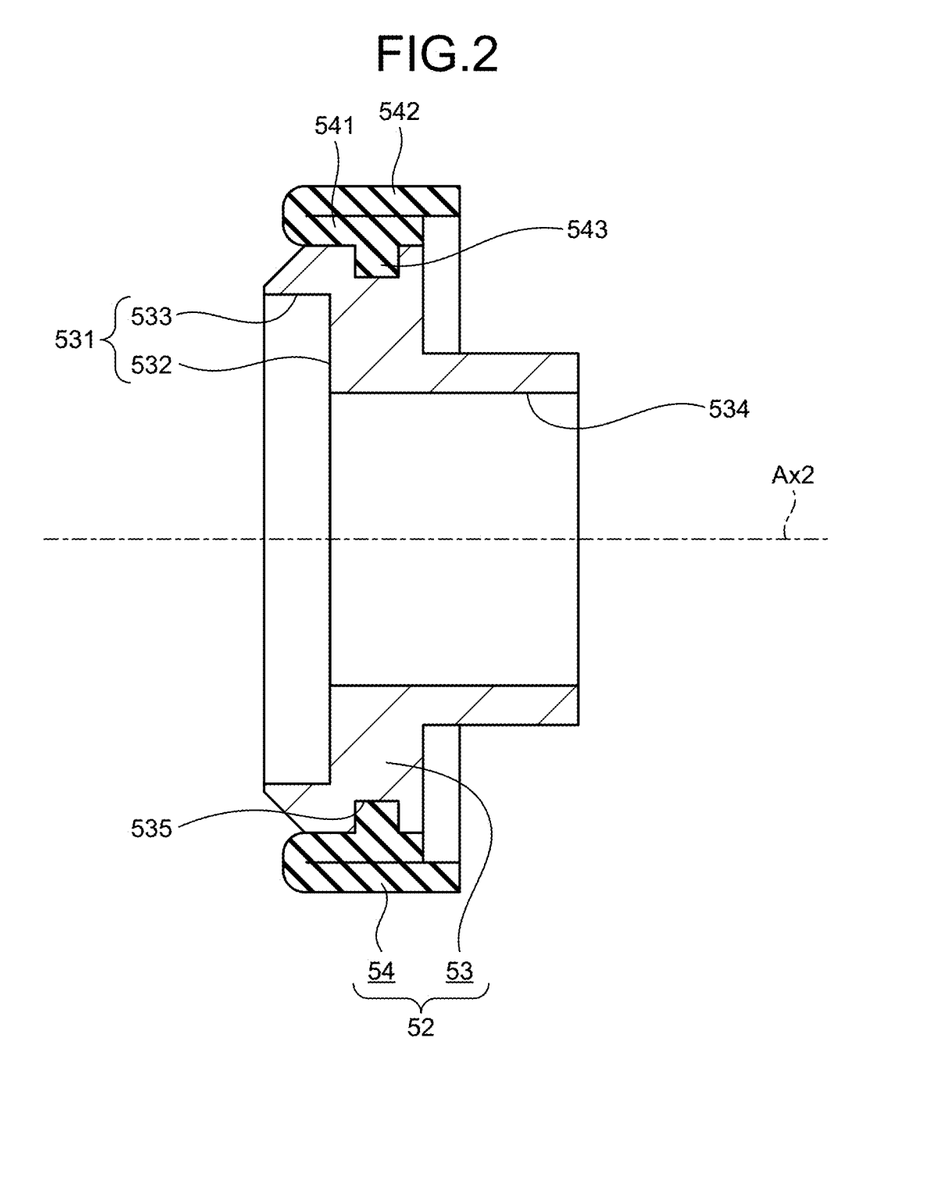
FIG. 2 illustrates the configuration of an endoscope connection portion.
Figure 3:
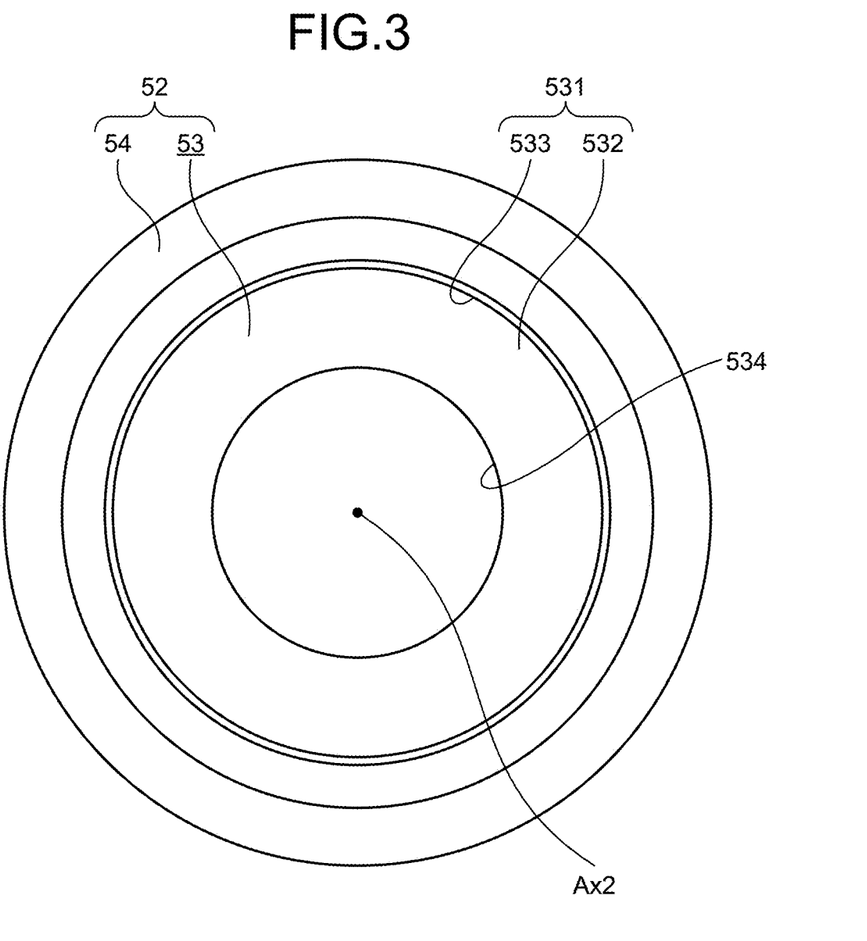
FIG. 3 illustrates the configuration of the endoscope connection portion.
Figure 4:
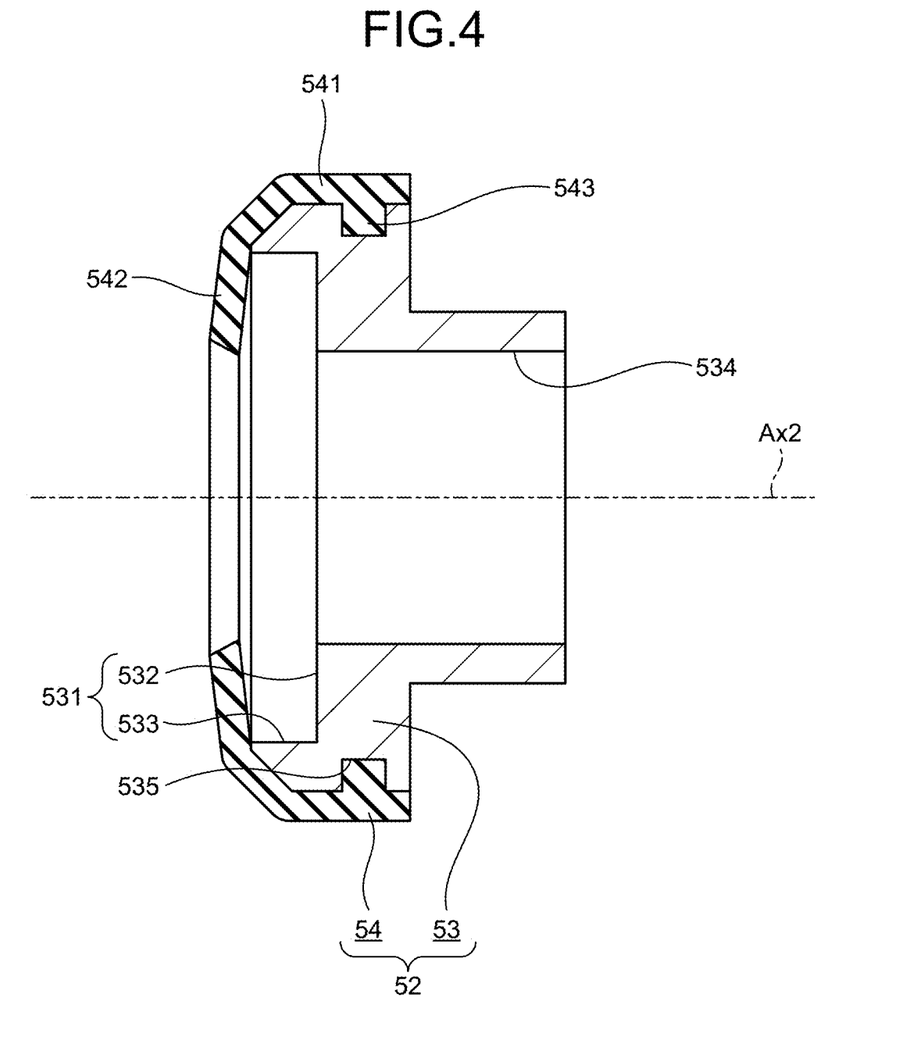
FIG. 4 illustrates the configuration of the endoscope connection portion.
Figure 5:
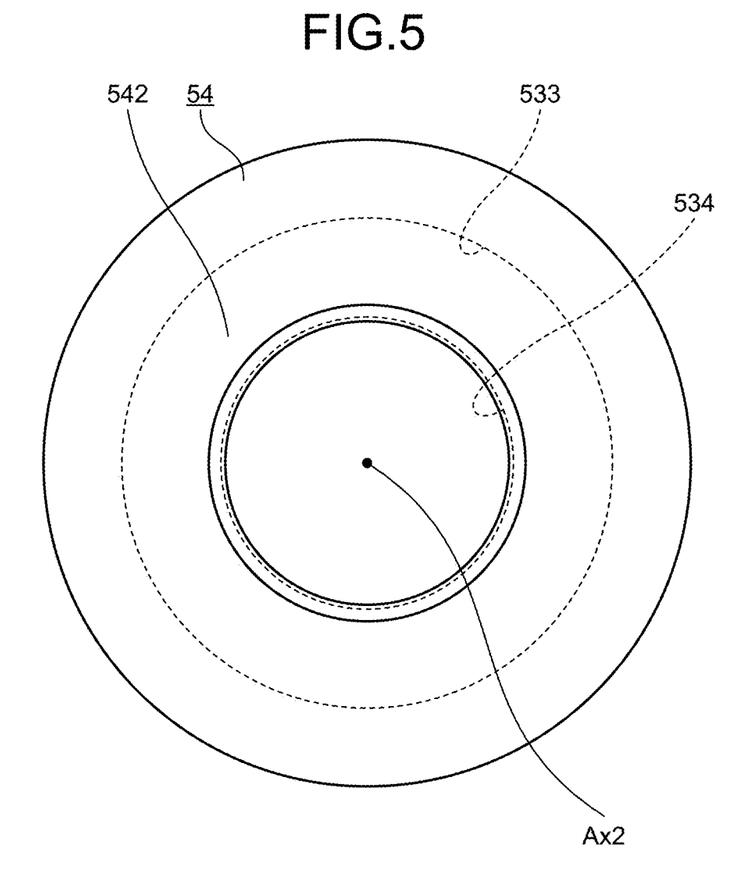
FIG. 5 illustrates the configuration of the endoscope connection portion.
Figure 6:
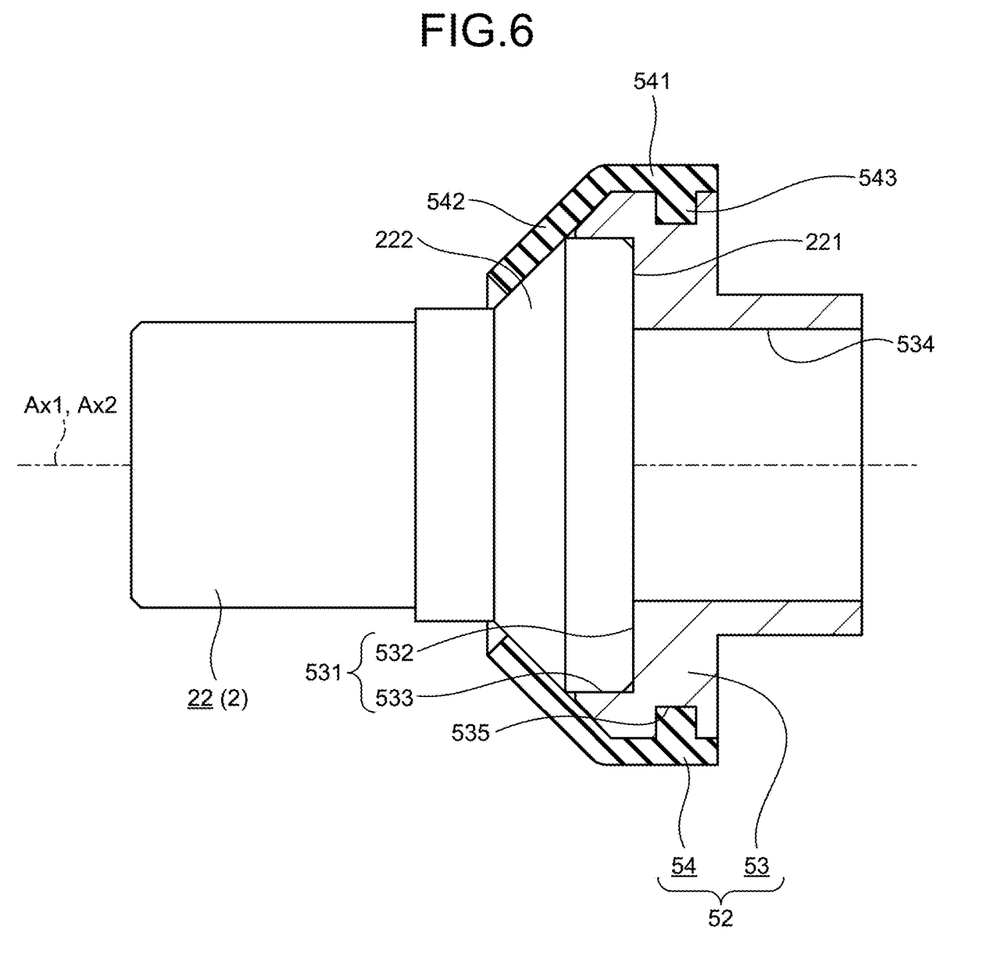
FIG. 6 illustrates the configuration of the endoscope connection portion.

FIGS. 2 to 6 illustrate the configuration of the endoscope connection portion 52. Specifically, FIG. 2 is a cross-sectional view of the endoscope connection portion 52 cut along a plane along the central axis Ax2 of the endoscope connection portion 52 with an elastic portion 54 being set in a first state. FIG. 3 illustrates the endoscope connection portion 52 seen from the distal end side with the elastic portion 54 being set in the first state. FIG. 4 is a cross-sectional view corresponding to FIG. 2, and illustrates a second state of the elastic portion 54. FIG. 5 illustrates the endoscope connection portion 52 seen from the distal end side with the elastic portion 54 being set in the second state. FIG. 6 illustrates the endoscope connection portion 52 connected to the eyepiece portion 22. Note that, in FIG. 6, only the endoscope connection portion 52 is cut along the plane along the central axis Ax2 for convenience of description.

First, before describing the configuration of the endoscope connection portion 52, the shape of the eyepiece portion 22 will be described.

The eyepiece portion 22 has a substantially cylindrical shape. In the following, the central axis of the eyepiece portion 22 will be referred to as the central axis Ax1 (FIG. 6).

As illustrated in FIG. 6, an end surface 221 on the proximal end side of the eyepiece portion 22 is flat and orthogonal to the central axis Ax1 (lens optical axis of the above-described eyepiece optical system).

Furthermore, as illustrated in FIG. 6, the distal end side on the outer peripheral surface of the eyepiece portion 22 has a tapered shape whose diameter decreases toward the distal end side. Hereinafter, the outer peripheral surface on the distal end side will be referred to as an inclined surface 222.

Next, the configuration of the endoscope connection portion 52 will be described.

As illustrated in FIGS. 2 to 6, the endoscope connection portion 52 includes a mounting portion 53 and the elastic portion 54.

The mounting portion 53 has a substantially columnar shape.

As illustrated in FIGS. 2 to 6, a mounting recess 531, which is depressed toward the proximal end side, is provided on an end surface on the distal end side of the mounting portion 53. The mounting recess 531 is a hole into which the eyepiece portion 22 is fitted when the camera head 5 (endoscope connection portion 52) is connected to the eyepiece portion 22. Hereinafter, the bottom surface of the mounting recess 531 will be referred to as an abutting surface 532 (FIGS. 2 to 4 and 6). The side surface of the mounting recess 531 will be referred to as a side surface 533 (FIGS. 2 to 6).

As illustrated in FIG. 2 to 4 or 6, the abutting surface 532 has a circular shape whose center coincides with the central axis Ax2. That is, the side surface 533 has an annular shape whose center coincides with the central axis Ax2. Furthermore, the abutting surface 532 is flat and orthogonal to the central axis Ax2. When the eyepiece portion 22 is fitted into the mounting recess 531, the end surface 221 on the proximal end side of the eyepiece portion 22 abuts on the abutting surface 532 in a direction along the central axis Ax1. Then, in the state where the eyepiece portion 22 is fitted into the mounting recess 531 (state where the camera head 5 (endoscope connection portion 52) is connected to the eyepiece portion 22), the central axes Ax1 and Ax2 match each other as illustrated in FIG. 6. That is, the abutting surface 532 functions as a positioning surface of the camera head 5 with respect to the endoscope 2 (positioning surface in the direction of the central axis Ax1 (Ax2) and positioning surface in rotation directions around two axes orthogonal to the central axis Ax1 (Ax2)).

Furthermore, as illustrated in FIGS. 2 to 6, an introduction hole 534 is provided on the mounting portion 53. The introduction hole 534 is a circular hole which penetrates from the end surface on the proximal end side to the abutting surface 532 and whose center coincides with the central axis Ax2.

The introduction hole 534 is used for introducing a subject image emitted from the eyepiece portion 22 into the sealing portion 51.

Moreover, as illustrated in FIG. 2, 4, or 6, an annular attachment groove 535 is provided on the outer peripheral surface of the mounting portion 53. The attachment groove 535 extends over the entire periphery in the peripheral direction around the central axis Ax2.

The elastic portion 54 is made of elastic material, and detachably attached to the mounting portion 53.

Note that examples of the elastic material include silicon rubber and Teflon (registered trademark) rubber.

In the first embodiment, the elastic portion 54 has a substantially cylindrical shape as illustrated in FIGS. 2 to 6. In the following, the elastic portion 54 is divided into two parts, one end side and the other end side. A part on one end side is described as a part 541 on one end side (FIGS. 2, 4, and 6). A part on the other end side is described as a part 542 on the other end side (FIGS. 2 and 4 to 6).

An annular attachment projection 543 is provided on the inner peripheral surface of the part 541 on one end side. The attachment projection 543 extends over the entire periphery in the peripheral direction around the central axis Ax2. Then, as illustrated in FIG. 4 or 5, the elastic portion 54 is attached to the mounting portion 53 by inserting a distal end portion of the mounting portion 53 into the part 541 on one end side and fitting the attachment projection 543 into the attachment groove 535. Note that, in the following, the state of the elastic portion 54 illustrated in FIGS. 4 and 5 is referred to as the second state.

Furthermore, the elastic portion 54 may be deformed from the second state (FIGS. 4 and 5) to the first state (FIGS. 2 and 3). In the second state, the elastic portion 54 is attached to the mounting portion 53. In the first state, the part 542 on the other end side is folded back toward the proximal end side (one end side), and thereby the outer peripheral surface of the part 541 on one end side is covered with the part 542 on the other end side.

Then, the camera head 5 (endoscope connection portion 52) is connected to the endoscope 2 (eyepiece portion 22) as illustrated below.

First, an operator sets the elastic portion 54 in the first state (FIGS. 2 and 3).

Next, the operator fits the eyepiece portion 22 into the mounting recess 531.

Then, the operator pulls the part 542 on the other end side of the elastic portion 54 set in the first state toward the distal end side, and applies the part 542 to the inclined surface 222. As illustrated in FIG. 6, this operation causes the elastic portion 54 to sandwich the eyepiece portion 22 between the part 542 on the other end side and the abutting surface 532 with the eyepiece portion 22 being inserted into the part 542 on the other end side, and biases the eyepiece portion 22 toward the abutting surface 532. Then, the endoscope connection portion 52 is connected to the eyepiece portion 22.

Note that, in consideration of biasing force (elastic force) of the elastic portion 54 biasing the eyepiece portion 22 and frictional resistance on the surface of the elastic portion 54, the endoscope 2 and the camera head 5 may relatively rotate around the central axis Ax1 (Ax2) with the endoscope 2 and the camera head 5 being connected with each other.

According to the above-described first embodiment, the following effects are exhibited.

The endoscope connection portion 52 constituting the camera head 5 according to the first embodiment includes the mounting portion 53 and elastic portion 54 described above. Here, the mounting portion 53 corresponds to a mount constituting a known endoscope connection portion. Furthermore, the elastic portion 54 corresponds to a ring constituting a known endoscope connection portion.

That is, in the endoscope connection portion 52 according to the first embodiment, the elastic portion 54 made of elastic material such as silicon rubber and Teflon rubber is adopted instead of a known ring. Thus, the weight of the camera head 5 may be reduced.

Furthermore, the elastic portion 54 may be attached to and detached from the mounting portion 53. That is, the elastic portion 54 may be a disposable portion that is disposed of after the usage of the camera head 5. Thus, the camera head 5 may be cleaned with the elastic portion 54 being detached from the mounting portion 53. Consequently, portions of the mounting portion 53 covered with the elastic portion 54 may also be satisfactorily cleaned.

From the above, according to the camera head 5 of the first embodiment, cleaning performance may be improved while weight is reduced.

In particular, the elastic portion 54 may be set in the first state (FIGS. 2 and 3). Thus, the camera head 5 (endoscope connection portion 52) may be smoothly attached to and detached from the endoscope 2 (eyepiece portion 22).

Next, a second embodiment will be described.

In the following description, the same signs are attached to configurations similar to those in the above-described first embodiment, and detailed description thereof will be omitted or simplified.

Figure 7:
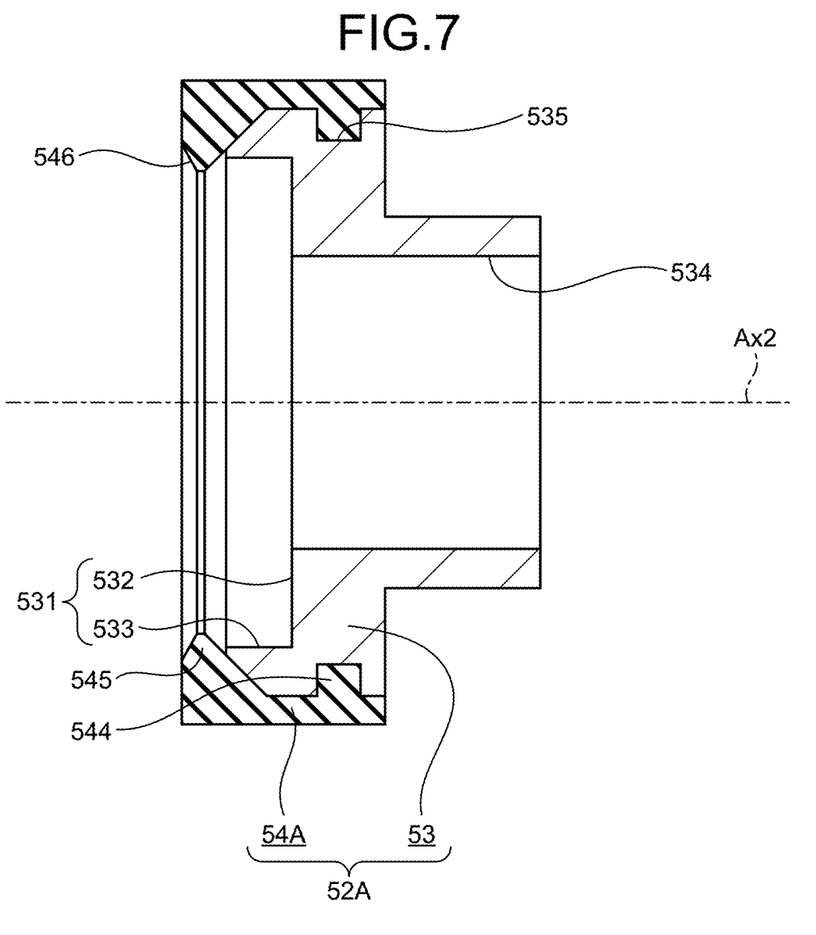
FIG. 7 illustrates the configuration of an endoscope connection portion according to a second embodiment.
Figure 8:
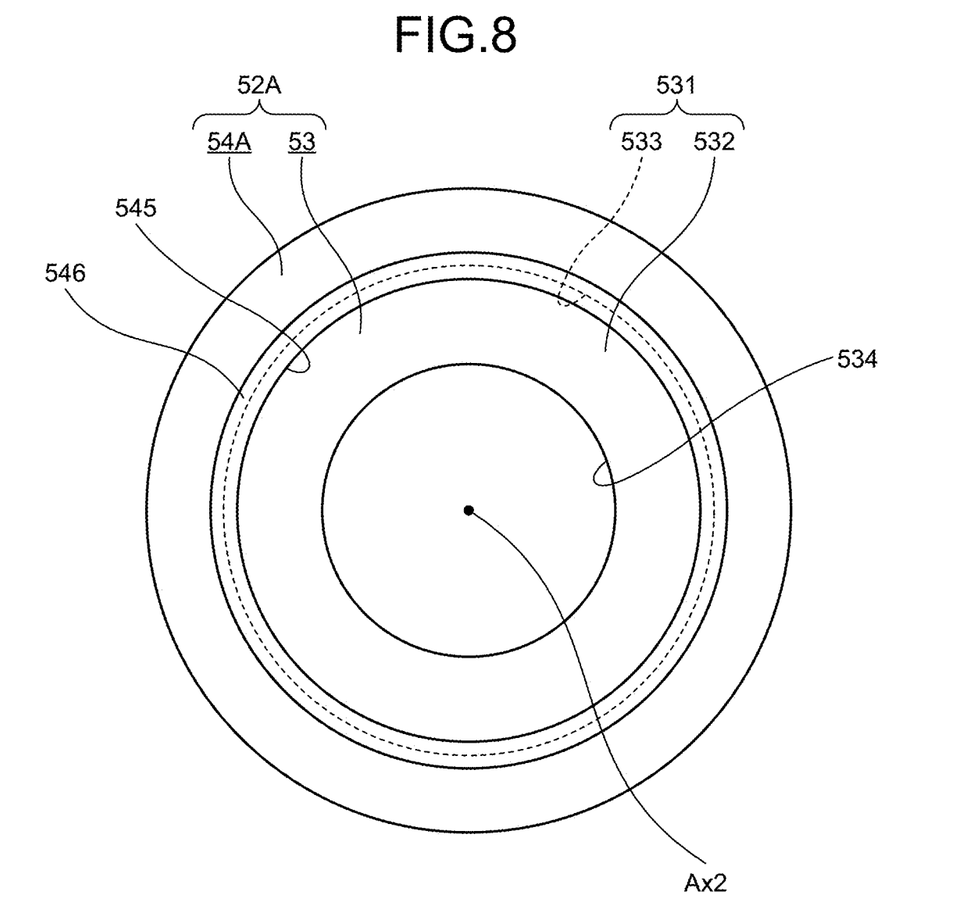
FIG. 8 illustrates the configuration of the endoscope connection portion according to the second embodiment.
Figure 9:
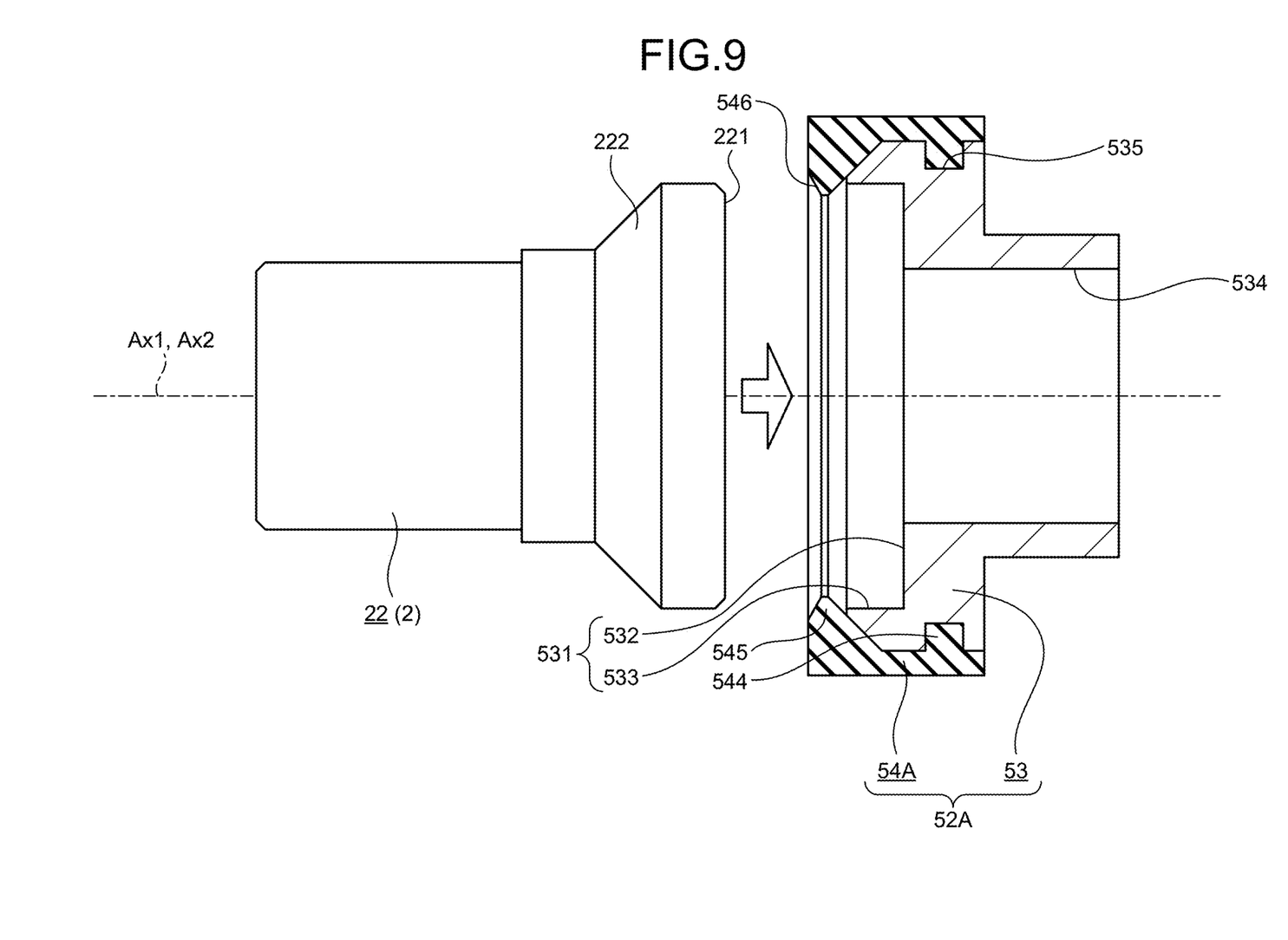
FIG. 9 illustrates the configuration of the endoscope connection portion according to the second embodiment.
Figure 10:
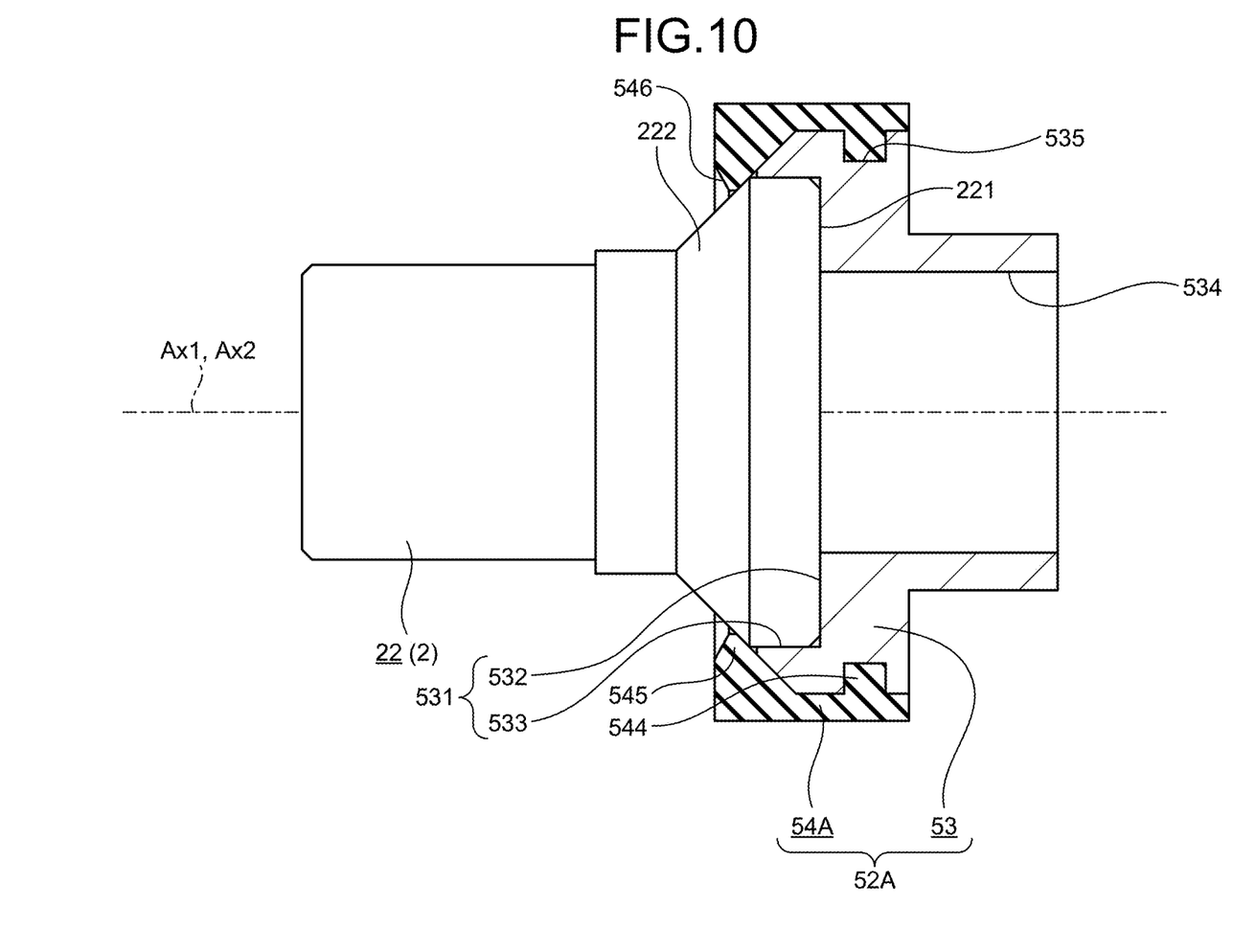
FIG. 10 illustrates the configuration of the endoscope connection portion according to the second embodiment.

FIGS. 7 to 10 illustrate the configuration of an endoscope connection portion 52A according to the second embodiment. Specifically, FIG. 7 is a cross-sectional view of the endoscope connection portion 52A cut along the plane along the central axis Ax2. FIG. 8 illustrates the endoscope connection portion 52A seen from the distal end side. FIG. 9 illustrates the endoscope connection portion 52A connected to the eyepiece portion 22. FIG. 10 illustrates the endoscope connection portion 52A connected to the eyepiece portion 22. Note that, in FIGS. 9 and 10, only the endoscope connection portion 52A is cut along the plane along the central axis Ax2 for convenience of description.

As illustrated in FIGS. 7 to 10, the endoscope connection portion 52A according to the second embodiment adopts an elastic portion 54A, which is different from the elastic portion 54, for the endoscope connection portion 52 described in the above-described first embodiment.

The elastic portion 54A is made of elastic material, and detachably attached to the mounting portion 53.

Note that examples of the elastic material constituting the elastic portion 54A include silicon rubber and Teflon rubber. The elastic material has higher rigidity than the elastic portion 54 described in the above-described first embodiment.

Then, the elastic portion 54A has a substantially cylindrical shape, similarly to the elastic portion 54 described in the above-described first embodiment.

As illustrated in FIG. 7, 9, or 10, an attachment projection 544 similar to the attachment projection 543 described in the above-described first embodiment is provided on the proximal end side on the inner peripheral surface of the elastic portion 54A. Then, as illustrated in FIGS. 7 to 10, the elastic portion 54A is attached to the mounting portion 53 by inserting a distal end portion of the mounting portion 53 from the proximal end side of the elastic portion 54A and fitting the attachment projection 543 into the attachment groove 535.

Furthermore, as illustrated in FIGS. 7 to 10, an annular claw portion 545 is provided on the distal end side on the inner peripheral surface of the elastic portion 54A. The claw portion 545 protrudes toward the central axis Ax2, and extends over the entire periphery in the peripheral direction around the central axis Ax2.

More specifically, the claw portion 545 is positioned on the distal end side more than the mounting portion 53. Then, as illustrated in FIG. 8, the ring formed at the protruding end of the claw portion 545 has a smaller diameter dimension than the side surface 533 of the mounting recess 531 when seen from the distal end side (positioned on the side close to the central axis Ax2).

Furthermore, as illustrated in FIGS. 7 to 10, an inclined surface 546 is formed on the end surface on the distal end side of the claw portion 545. The inclined surface 546 is inclined so as come close to the central axis Ax2 toward the proximal end side.

Then, the endoscope connection portion 52A is connected to the eyepiece portion 22 as illustrated below.

First, as illustrated in FIG. 9, an operator moves the eyepiece portion 22 and the endoscope connection portion 52A in a direction of coming close to each other. Then, the operator applies the end surface 221 on the proximal end side of the eyepiece portion 22 to the inclined surface 546. Furthermore, the operator further moves the eyepiece portion 22 and the endoscope connection portion 52A in a direction of coming close to each other. This causes the claw portion 545 to be pressed by the eyepiece portion 22 and moved in a direction away from the central axis Ax2 by elastic deformation of the elastic portion 54A. Furthermore, when the claw portion 545 is located at a position facing the inclined surface 222 in the radial direction while sliding on the outer surface of the eyepiece portion 22, the claw portion 545 sandwiches the eyepiece portion 22 with the abutting surface 532, and biases the eyepiece portion 22 toward the abutting surface 532 by reaction force that tries to return to the original shape. Then, the endoscope connection portion 52A is connected to the eyepiece portion 22. That is, in the second embodiment, a so-called snap-fit type configuration is adopted as a configuration for connection to the eyepiece portion 22.

Note that, in consideration of biasing force (elastic force) of the elastic portion 54A biasing the eyepiece portion 22 and frictional resistance on the surface of the elastic portion 54A, similarly to the above-described first embodiment, the endoscope 2 and the camera head 5 may relatively rotate around the central axis Ax1 (Ax2) with the endoscope 2 and the camera head 5 being connected with each other.

According to the above-described second embodiment, the following effect is exhibited in addition to similar effects in the above-described first embodiment.

In the endoscope connection portion 52A according to the second embodiment, the claw portion 545 is provided in the elastic portion 54A, and a so-called snap-fit type connection structure is adopted. Thus, the endoscope connection portion 52A may be more smoothly attached to and detached from the eyepiece portion 22.

Next, a third embodiment will be described.

In the following description, the same signs are attached to configurations similar to those in the above-described second embodiment, and detailed description thereof will be omitted or simplified.

Figure 11:
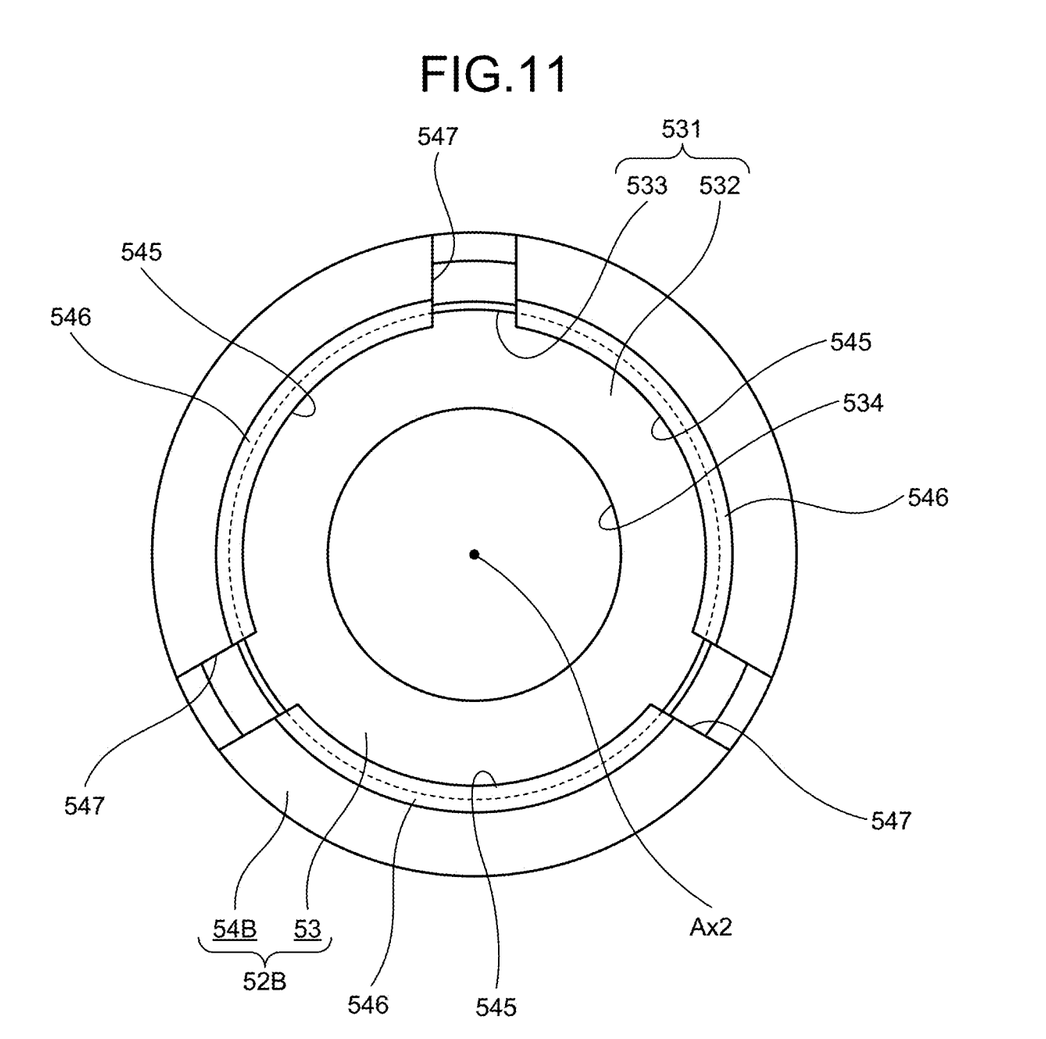
FIG. 11 illustrates the configuration of an endoscope connection portion according to a third embodiment.

FIG. 11 illustrates the configuration of an endoscope connection portion 52B according to the third embodiment. Specifically, FIG. 11 illustrates the endoscope connection portion 52B seen from the distal end side.

As illustrated in FIG. 11, the endoscope connection portion 52B according to the third embodiment adopts an elastic portion 54B, which is different from the elastic portion 54A, for the endoscope connection portion 52A described in the above-described second embodiment.

As illustrated in FIG. 11, the elastic portion 54B is different from the elastic portion 54A described in the above-described second embodiment in that a plurality of (three in the example of FIG. 11) cut portions 547 is provided from the distal end to the proximal end.

Three cut portions 547 are provided at positions rotationally symmetric by 120° around the central axis Ax2.

That is, as a result of providing the three cut portions 547, the claw portions 545 are also provided at positions rotationally symmetric by 120° around the central axis Ax2.

Note that a method of connecting the endoscope connection portion 52B to the eyepiece portion 22 is similar to that in the above-described second embodiment.

According to the above-described third embodiment, the following effect is exhibited in addition to a similar effect in the above-described second embodiment.

In the endoscope connection portion 52B according to the third embodiment, a plurality of claw portions 545 is provided along the peripheral direction around the central axis Ax2. Thus, the claw portion 545 may be moved with weaker force in accordance with the elastic deformation of the elastic portion 54B. The endoscope connection portion 52B may be more smoothly attached to and detached from the eyepiece portion 22.

Although the embodiments for carrying out the disclosure have been described so far, the disclosure should not be limited only by the above-described embodiments.

Although, in the above-described first to third embodiments, the abutting surface 532 is defined as the bottom surface of the mounting recess 531, this is not a limitation. For example, when a plurality of projections is provided on the bottom surface of the mounting recess 531, a flat surface formed at each protruding end of the plurality of projections may be used as an abutting surface according to the disclosure.

According to a camera head of the disclosure, cleaning performance may be improved while weight is reduced.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A camera head comprising:
a mounting portion having an abutting surface on which an eyepiece portion of an endoscope abuts in a direction along an optical axis of a subject image emitted from the eyepiece portion; and
an elastic portion including elastic material and detachably attached to the mounting portion, the elastic portion being configured to sandwich the eyepiece portion with the abutting surface, and bias the eyepiece portion toward the abutting surface wherein the elastic portion includes a cylinder, wherein the elastic portion is allowed to be deformed to have a shape in which an outer peripheral surface of a part on one end side is covered with a part on the other end side by folding back the part on the other end side toward one end side with the elastic portion being attached to the mounting portion.

2. The camera head according to claim 1, wherein the elastic portion being attached to the mounting portion with the mounting portion being inserted into the part on one end side, and configured to
sandwich the eyepiece portion between the part on another end side and the abutting surface with the eyepiece portion being inserted into the part on the other end side, and bias the eyepiece portion toward the abutting surface.

3. The camera head according to claim 1, wherein the mounting portion includes a first mating portion and the elastic portion includes a second mating portion corresponding to the first mating portion to mate the elastic portion to the mounting portion.

4. The camera head according to claim 3, wherein the first mating portion is a groove and the second mating portion is a protrusion.

5. A camera head comprising:
a mounting portion having an abutting surface on which an eyepiece portion of an endoscope abuts in a direction along an optical axis of a subject image emitted from the eyepiece portion; and
an elastic portion including elastic material and detachably attached to the mounting portion, wherein
an end surface of the elastic portion includes an inclined surface inclined toward the optical axis toward a proximal end side,
the inclined surface of the elastic portion being configured to sandwich the eyepiece portion with the abutting surface, and bias the eyepiece portion toward the abutting surface, and
the elastic portion is allowed to be deformed to have a shape in which an outer peripheral surface of a part on one end side is covered with a part on the other end side by folding back the part on the other end side toward one end side with the elastic portion being attached to the mounting portion, wherein, when the other end side if unfolded, the other end side has the inclined surface.

6. The camera head according to claim 5, wherein the mounting portion includes a first mating portion and the elastic portion includes a second mating portion corresponding to the first mating portion to mate the elastic portion to the mounting portion.

7. The camera head according to claim 5, wherein the elastic portion including a cylinder, the elastic portion being attached to the mounting portion with the mounting portion being inserted into the part on one end side, and configured to
sandwich the eyepiece portion between the part on another end side and the abutting surface with the eyepiece portion being inserted into the part on the other end side,
and bias the eyepiece portion toward the abutting surface.

8. The camera head according to claim 7, wherein, when the elastic portion is deformed from a second state in which to receive the eyepiece portion to a first state, the elastic portion is allowed to be deformed to have the shape in which the outer peripheral surface of the part on one end side is covered with the part on the other end side by folding back the part on the other end side toward one end side with the elastic portion being attached to the mounting portion.

9. A camera head comprising:
a mounting portion having an abutting surface on which an eyepiece portion of an endoscope abuts in a direction along an optical axis of a subject image emitted from the eyepiece portion; and
an elastic portion including elastic material and detachably attached to the mounting portion, wherein
an end surface of the elastic portion includes an inclined surface inclined toward the optical axis toward a proximal end side,
the inclined surface of the elastic portion being configured to sandwich the eyepiece portion with the abutting surface, and bias the eyepiece portion toward the abutting surface,
the mounting portion includes a first mating portion and the elastic portion includes a second mating portion corresponding to the first mating Portion to mate the elastic portion to the mounting portion, and
the first mating portion is a groove and the second mating portion is a protrusion.

* * * * *